United States Patent [19]

Karol

[11] Patent Number: 5,138,065
[45] Date of Patent: Aug. 11, 1992

[54] POLYETHER GLYCOL DERIVATIVES OF 2,5-DIMERCAPTO-1,3,4-THIADIAZOLE

[75] Inventor: Thomas J. Karol, Norwalk, Conn.

[73] Assignee: R. T. Vanderbilt Company, Inc., Norwalk, Conn.

[21] Appl. No.: 698,006

[22] Filed: May 9, 1991

[51] Int. Cl.$^5$ ............... C07D 285/125; C10M 135/36
[52] U.S. Cl. .................................. 548/142; 252/47.5
[58] Field of Search ........................ 548/142; 252/47.5

[56] References Cited

U.S. PATENT DOCUMENTS

| | | | |
|---|---|---|---|
| 3,980,573 | 9/1976 | Okorodudu | 252/46.7 |
| 4,140,643 | 2/1979 | Davis | 252/47.5 |
| 4,902,804 | 2/1990 | King et al. | 548/130 |
| 5,055,584 | 10/1991 | Karol | 548/142 |

FOREIGN PATENT DOCUMENTS

| | | |
|---|---|---|
| 0218816 | 4/1987 | European Pat. Off. |
| 0223916 | 6/1987 | European Pat. Off. |
| 0289964 | 11/1988 | European Pat. Off. |
| 1462287 | 1/1977 | United Kingdom |

*Primary Examiner*—Robert Gerstl
*Attorney, Agent, or Firm*—Rasma B. Balodis

[57] ABSTRACT

Disclosed are novel compounds prepared by reacting molar equivalents of polyether glycol with maleic anhydride and then reacting the intermediate with 2,5-dimercapto-1,3,4-thiadiazole. The compounds are dispersants or detergents, antiwear agents and antioxidants when incorporated into lubricating compositions.

4 Claims, No Drawings

POLYETHER GLYCOL DERIVATIVES OF 2,5-DIMERCAPTO-1,3,4-THIADIAZOLE

BACKGROUND OF THE INVENTION

The present invention concerns novel polyether glycol derivatives of 2,5-dimercapto-1,3,4-thiadiazoles and their use as multifunctional additives for lubricating compositions.

Lubricating compositions ordinarily are formulated with various additives to enhance their performance. A problem sometimes encountered is that of compatibility between the various additives used. Therefore, it is desirable to use lubricating additives that can perform different functions.

Another occurring problem is that a particular additive or a combination of additives decreases the solubility of other additives in the lubricating composition resulting in undesirable haze or sediment formation. Dispersants or detergents are added to alleviate the problem.

Generally, lubricants contain additives known as antiwear agents which increase the load-carrying capacity of lubricants. The antiwear additives promote the formation of a surface film and thereby prevent wear of the contacting metal surfaces. During the course of use, lubricants are susceptible to deterioration due to oxidation. The oxidative process leads to the loss of lubricating properties and inadequate protection of the device to be lubricated. Antioxidants are added to inhibit the oxidative process. Therefore, it is desirable that antiwear agents possess antioxidant properties.

U.S. Pat. No. 4,140,643 describes a mixed reaction product which is rendered oil-soluble by reacting an oil-soluble dispersant with 2,5-dimercapto-1,3,4-thiadiazole and then reacting the intermediate with a carboxylic acid. British Pat. No. 1,462,287 describes multipurpose additives prepared by reacting the dimercaptothiadiazole with an oil-soluble dispersant.

It has been discovered that certain polyether glycol derivatives of 2,5-dimercapto-1,3,4-thiadiazoles display dispersant as well as antiwear and antioxidant properties.

SUMMARY OF THE INVENTION

In accordance with the invention, there are provided novel 1,3,4-thiadiazole compounds characterized by the structural formula

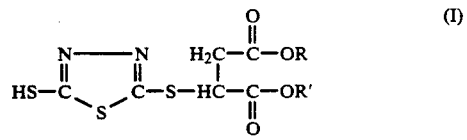

wherein R represents aliphatic polyether glycol residue and R' represents hydrogen and aliphatic alcohol residue having 1 to 8 carbon atoms.

Another aspect of the invention concerns improved oil-based lubricating compositions comprising a major amount of base oil and an effective amount to impart antiwear and antioxidant properties to said composition, of a 1,3,4-thiadiazole characterized by the formula I.

A further aspect of the invention concerns a method for protection of metal surfaces from wear by applying improved lubricating oil compositions, the improvement of which consists of adding to the composition an effective amount of a 1,3,4-thiadiazole characterized by the structural formula I.

DESCRIPTION OF SPECIFIC EMBODIMENTS

The novel compounds of the invention may be prepared by reacting molar equivalents of polyether glycol with maleic anhydride and then reacting the intermediate with 2,5-dimercapto-1,3,4-thiadiazole to yield the structurally defined compounds of formula I. A general reaction scheme is given below.

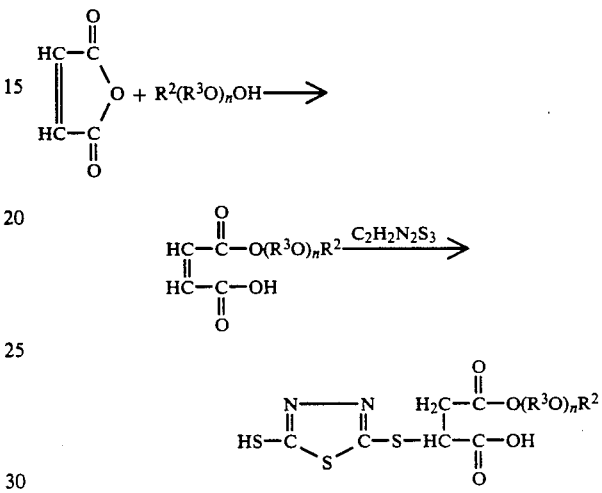

wherein $R^2$ and $R^3$ represent aliphatic chain.

The polyether glycols useful to the invention are terminated by at least one alcohol end group. The compounds have the general formula $R^2(R^3O)_nOH$. The $R^2$ group may be a hydroxy group or an aliphatic group. The aliphatic group may be straight or branched chain and may contain up to 8 carbon atoms. The $R^3O$ unit may be selected from straight or branched chain alkylene oxide groups, as for example ethylene oxide, propylene oxide, isopropylene oxide, butylene oxide, isobutylene oxide, pentylene oxide and similar units forming poly(alkylene glycol) products. Various polymeric glycols are available commercially. The polymers may range in average molecular weight from 340 to 4000 and higher. The preferred polymer range is dependent on the lubrication medium and on the additives used therein. For greases, where solubility and dispersancy/detergency are of low concern and higher antioxidant and load-carrying properties are required, the preferred molecular weight range is 340 to 1000. In two-cycle motor oils where the base oil is vegetable or synthetic in nature, the preferred molecular weight range is 950 to 2500. For two-cycle motor oils where the base is mineral oil, the preferred molecular weight is 950 to 4000. For general lubricants using mineral oil, the preferred molecular weight is 1500 to 4000.

The aliphatic alcohol residue R' of formula I is preferably selected from alcohols having 1 to 8 carbon atoms. Representative alcohols include, among others, methanol, butanol, n-octanol and 2-ethylhexanol.

The thiadiazole derivatives of the invention are useful as additives for industrial lubricating compositions and engine oil formulations as for example two cycle oils used in internal combustion engines.

The thiadiazole compounds possess multifunctional properties. They perform antiwear and oxidation inhibiting functions and are effective dispersants in lubricants or, namely, detergents in engine oils. The dispersant property of the compounds facilitates their incorporation into the oil compositions and contributes to the overall stability and performance of the oil composition.

The lubricating compositions contemplated herein include lubricating oils, engine oils and lubricating greases containing a major amount of base oil. The base oil may be selected from naphthenic, aromatic, paraffinic, mineral, vegetable and synthetic oils. The synthetic oils may be selected from, among others, alkylene polymers, polysiloxanes, di-, tri- and tetraester-type oils, and carboxylic acid esters.

The amount of the thiadiazole additive required to be effective for imparting antiwear and antioxidant characteristics to lubricating compositions may range from about 0.01 to 15.0 percent of the additive based on the lubricating composition.

The lubricating compositions may contain the necessary ingredients to formulate the composition, as for example emulsifiers, other dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

The following examples are given for the purpose of further illustrating the invention. All percentages and parts are based on weight unless otherwise indicated.

EXAMPLE 1

A reactor was charged with polypropylene glycol monobutyl ether, 147 g (0.095 moles) and maleic anhydride, 8.88 g (0.091 moles), heated to 135°–141° C. with stirring and reacted for one hour. 2,5-Dimercapto-1,3,4-thiadiazole, 13.6 g (0.091 moles) was charged to the reactor and the reaction was maintained at 135°–141° C. for one hour. The reaction product was filtered with a filter aid. The product was a light yellow liquid.

EXAMPLE 2

A reactor was charged with polypropylene glycol monobutyl ether, (1500 mol. weight) 775 g and maleic anhydride, 49.5 g, heated to 100° C. for 1 hour and allowed to stand overnight. After stripping off maleic anhydride, 2-ethylhexanol, 65 g, 70 percent methanesulfonic acid, 3.5 ml, and azeotropic mixed hexane/heptane solvent were added and the reaction was refluxed at 130° to 140° C. The reactor was fitted with a Dean Stark trap filled with the solvent and water was removed. 2,5-Dimercapto-1,3,4-thiadiazole, 80 g, was charged and the reaction was heated at 135° to 140° C. for 1 hour. The reaction was stirred for 2 hours with sodium bicarbonate, allowed to stand overnight, stripped and filtered.

EXAMPLE 3

Four-Ball Wear Test

The test was conducted essentially according to the method described in the UNITED STATES STEEL LUBRICATION ENGINEERS MANUAL, 134 (1st ed., 1971). Four highly polished steel balls 12.5 mm in diameter were placed in a test cup and submerged in the test sample. The base oils were castor oil and synthetic diester base, Emery® 2958 manufactured by Emery Industries Inc. The test was carried out at a rotation speed of 1800 rpm under a load of 20 kg at 54.4° C. for 60 minutes. The diameter of wear scar produced by the base oil and the test sample containing the additive prepared in Example 1 was measured. The data compiled in Table I indicate that the additive of the invention has good antiwear properties.

TABLE I

| | Four-Ball Wear Test | | | |
| | Compositions, Percent | | | |
| | 1 | 2 | 3 | 4 |
| Components | | | | |
| Diester Base | 100 | 99.0 | — | — |
| Castor Oil | — | — | 100 | 99.0 |
| Product of Example 1 | — | 1.0 | — | 1.0 |
| Physical Properties | | | | |
| Scar diameter, m | 0.78 | 0.54 | 0.68 | 0.39 |

EXAMPLE 4

Rotary Bomb Oxygen Uptake Test

The oxidation induction time of lubricating compositions was measured under conditions which simulate the high temperature, severe oxidation processes in engines by a rotary bomb oxidation test method ASTM D-2272. The test was conducted with 50 g samples at 150° C. and initial oxygen pressure of 620.6 kPa (90 psi). The lubricant bases described in Example 3 contained no water. A "pass" oil has a high induction time, while a "fail" oil has a low induction time. The data compiled in Table II demonstrate oxidation inhibition characteristics of the compound of the invention.

TABLE II

| | Rotary Bomb Oxygen Utake | |
| | Compositions, Percent | |
| | 5 | 6 |
| Components | | |
| Diester Base | 100 | 99.0 |
| Product of Example 1 | — | 1.0 |
| Physical Properties | | |
| Average Induction Time, Min. | 45 | 175 |

The product of Example 1 was evaluated in a prototype castor oil-based two-cycle motor oil. Long-term engine fleet tests have indicated that the compound has good detergent properties and inhibits sediment formation on the engine parts.

The above embodiments have shown various aspects of the present invention. Other variations will be evident to those skilled in the art and such modifications are intended to be within the scope of the invention as defined by the appended claims.

What is claimed is:

1. A thiadiazole compound selected from the group of compounds having the structural formula

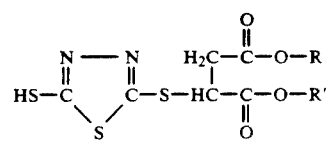

wherein R represents aliphatic polyether glycol residue having the formula —$(R^3O)_nR^2$ wherein $R^2$ represents hydrogen and an alkyl group having 1 to 8 carbon atoms, $R^3$ represents an alkyl group having 1 to 8 carbon atoms and n represents a unit number to yield an average molecular weight of the residue ranging from 340 to 4000, and R' represents hydrogen and aliphatic alcohol residue having 1 to 8 carbon atoms.

2. A compound according to claim 1 wherein the glycol residue is polypropylene glycol monobutyl ether.

3. A lubricating composition comprising a major portion of natural or synthetic oil of lubricating viscosity and a minor antiwear and oxidation inhibiting amount of a compound selected from the group consisting of compounds having the structural formula

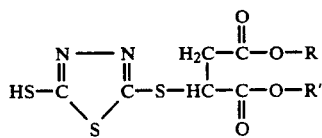

wherein R represents aliphatic polyether glycol residue having the formula —$(R^3O)_nR^2$ wherein $R^2$ represents hydrogen and an alkyl group having 1 to 8 carbon atoms, $R^3$ represents an alkyl group having 1 to 8 carbon atoms and n represents a unit number to yield an average molecular weight of the residue ranging from 340 to 4000, and R' represents hydrogen and aliphatic alcohol residue having 1 to 8 carbon atoms.

4. A method for protecting metal surfaces from wear which comprises contacting the surfaces with a lubricating composition comprising a major amount of base oil of lubricating viscosity, the improvement of which consists of adding to the oil a minor antiwear and oxidation inhibiting amount of an additive selected from the group of compounds having the structural formula

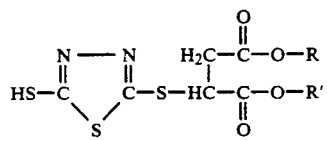

wherein R represents aliphatic polyether glycol residue having the formula —$(R^3O)_nR^2$ wherein $R^2$ represents hydrogen and an alkyl group having 1 to 8 carbon atoms, $R^3$ represents an alkyl group having 1 to 8 carbon atoms and n represents a unit number to yield an average molecular weight of the residue ranging from 340 to 4000, and R' represents hydrogen and aliphatic alcohol residue having 1 to 8 carbon atoms.

* * * * *